(12) United States Patent
Butlin et al.

(10) Patent No.: US 7,626,020 B2
(45) Date of Patent: Dec. 1, 2009

(54) PROTECTED FORMS OF N-(3-METHOXY-5-METHYLPIPERAZIN-2-YL)-2-(4-[1,3,4,-OXADIAZOL-2-YL]PHENYL)-PYRIDINE-3-SULPHONAMIDE

(75) Inventors: Margaret Anne Butlin, Macclesfield (GB); Roger John Butlin, Macclesfield (GB); Philip John Hogan, Macclesfield (GB); Andreas Meudt, Sulzbach (DE)

(73) Assignee: AstraZeneca AB, Sodertalje (SE)

( * ) Notice: Subject to any disclaimer, the term of this patent is extended or adjusted under 35 U.S.C. 154(b) by 329 days.

(21) Appl. No.: 10/598,116

(22) PCT Filed: Feb. 17, 2005

(86) PCT No.: PCT/GB2005/000567

§ 371 (c)(1),
(2), (4) Date: Aug. 17, 2006

(87) PCT Pub. No.: WO2005/080403

PCT Pub. Date: Sep. 1, 2005

(65) Prior Publication Data

US 2008/0161565 A1     Jul. 3, 2008

(30) Foreign Application Priority Data

Feb. 20, 2004 (GB) .................. 0403744.6

(51) Int. Cl.
    *C07F 9/02* (2006.01)
(52) U.S. Cl. ..................................... 544/337
(58) Field of Classification Search ........... None
    See application file for complete search history.

(56) References Cited

U.S. PATENT DOCUMENTS

| | | | |
|---|---|---|---|
| 5,464,853 A | 11/1995 | Chan et al. | |
| 5,514,691 A | 5/1996 | Chan et al. | |
| 5,843,902 A | 12/1998 | Garnick et al. | |
| 6,197,967 B1 | 3/2001 | Vollmueller et al. | |
| 2002/0055457 A1 | 5/2002 | Janus et al. | |
| 2002/0107284 A1 | 8/2002 | Uckun et al. | |
| 2003/0092757 A1 | 5/2003 | Singh et al. | |
| 2005/0014769 A1 | 1/2005 | Osswald et al. | |

FOREIGN PATENT DOCUMENTS

| | | |
|---|---|---|
| EP | 0510526 A1 | 10/1992 |
| EP | 0526708 A1 | 2/1993 |
| EP | 0558258 A1 | 9/1993 |
| EP | 0569193 A1 | 11/1993 |
| EP | 0640596 A1 | 3/1995 |
| EP | 0682016 A1 | 11/1995 |
| EP | 0749964 A1 | 12/1996 |
| EP | 1256344 A1 | 11/2002 |
| EP | 1424080 A1 | 6/2004 |
| GB | 2295616 A1 | 6/1996 |
| WO | 94/27979 A1 | 12/1994 |
| WO | 95/26957 A1 | 10/1995 |
| WO | 96/09818 A1 | 4/1996 |
| WO | 96/40681 A1 | 12/1996 |
| WO | 98/40332 A1 | 9/1998 |
| WO | 99/48530 A1 | 9/1999 |
| WO | 99/55683 A1 | 11/1999 |
| WO | 99/56761 A1 | 11/1999 |
| WO | 00/21509 A2 | 4/2000 |
| WO | 00/36918 A1 | 6/2000 |
| WO | 00/67024 A1 | 11/2000 |
| WO | 01/00198 A2 | 1/2001 |
| WO | 01/44239 A2 | 6/2001 |
| WO | 01/60370 A1 | 8/2001 |
| WO | 01/91736 A2 | 12/2001 |
| WO | 02/11713 A2 | 2/2002 |
| WO | 02/49630 A2 | 6/2002 |
| WO | 02/069906 A2 | 9/2002 |
| WO | 02/074034 A2 | 9/2002 |
| WO | 02/080960 A2 | 10/2002 |
| WO | 02/085351 A1 | 10/2002 |
| WO | 03/006041 A1 | 1/2003 |
| WO | 03/009805 A2 | 2/2003 |
| WO | 03/015820 A1 | 2/2003 |
| WO | 03/039539 A2 | 5/2003 |
| WO | 03/045434 A2 | 6/2003 |
| WO | 2004/018044 A2 | 3/2004 |
| WO | 2004/032922 A1 | 4/2004 |
| WO | 2004/035057 A1 | 4/2004 |
| WO | 2005/023264 A1 | 3/2005 |
| WO | 2005/063735 A1 | 7/2005 |
| WO | 2006/056760 A1 | 6/2006 |
| WO | 2007/010235 A1 | 1/2007 |

OTHER PUBLICATIONS

Dorwald F. A. Side Reactions in Organic Synthesis, 2005, Wiley: VCH, Weinheim p. IX of Preface.*

(Continued)

*Primary Examiner*—James O Wilson
*Assistant Examiner*—Jeffrey H Murray

(57) ABSTRACT

The invention relates to compounds such as

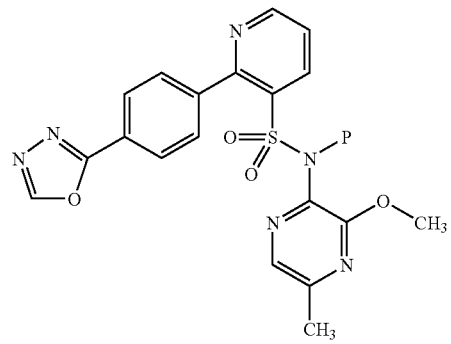

where P is a nitrogen-protecting group, and to processes for preparing these compounds.

6 Claims, No Drawings

OTHER PUBLICATIONS

Morris, Michael J. et al., Clinical approaches to osseous metastases in prostate cancer, The Oncologist, 2003, pp. 161-173, vol. 8, No. 2.
Rosano, Laura A. et al., Therapeutic targeting of the endohelin a receptor in human ovarian carcinoma, Cancer Research, May 15, 2003, pp. 2447-2453, vol. 63, No. 10, XP002365689.
Walczak J. R. et al., Pharmacological Treatments for Prostate Cancer, Expert Opinion on Investigational Drugs, 2002, pp. 1737-1748, vol. 11, No. 12, XP009008862.
Rosano, Laura et al., ZD4054, a specific antagonist of the endothelin A receptor, inhibits tumor growth and enhances cytotoxicity of paclitaxel in human ovarian carcinoma in vitro and in vivo, Apr. 16-20, 2005, AACR, Anaheim/Orange County, CA.
Curtis, N. et al., ZD4054 specifically inhibits endothelin A receptor-mediated anti-apoptotic effects, but not endothelin B receptor-mediated pro-apoptotic effects, Sep. 28-Oct. 1, 2004, AACR-NCI-EORTC, Geneva, Switzerland.
Liu, Glenn et al., Tolerability profile of ZD4054 is consistent with the effects of endothelin A receptor-specific antagonism, May 13-17, 2005, ASCO Annual Meeting, Orlando, Florida.
Morris, C. et al., ZD4054: specificity for endothelin A receptor following single-dose administration in healthy volunteers, Sep. 28-Oct. 1, 2004, AACR-NCI-EORTC, Geneva, Switzerland.
Dreicer, R. et al., ZD4054 specifically inhibits endothelin A receptor-mediated effects but not endothelin B receptor-mediated effects, Feb. 17-19, 2005, ASCO Prostate Cancer Symposium, Orlando, Florida.
Todd, Martin et al., Metabolite Factories: Use of microbial systems to generate metabolites of an endothelin receptor antagonist, Jul. 3-8, 2005, Biotrans 2005, Delft, The Netherlands.
Morris, C.D. et al., Specific inhibition of the endothelin A receptor with ZD4054: clinical and preclinical evidence, British Journal of Cancer, 2005, 2148-2152, vol. 92.
Curtis, N. et al., ZD4054 blocks ET-1-stimulated phosphorylation of p44/42 mitogen-activated protein kinase and proliferation of osteoblast cells, Apr. 16-20, 2005, AACR, Anaheim/Orange County, CA.
Morris, C.D. et al, ZD4054 reduces endothelin-1-induced forearm vasoconstriction in healthy male volunteers, Apr. 16-20, 2005, AACR, Anaheim/Orange County, CA.
Rosano, Laura et al, Combined targeting of the endothelin receptor and the epidermal growth factor receptor in ovarian cancer shows enhanced antiproliferative effects, Apr. 1-5, 2006, AACR 2006, Washington, DC.
Curwen, J.O., ZD4054 : A specific endothelin A receptor antagonist with potential utility in prostate cancer and metastatic bone disease, European Journal of Cancer, Nov. 2002, p. S102, vol. 38, XP004403782.
Nelson, J.B., The role of endothelin-1 and endothelin receptor antagonists in prostate cancer, British Journal of Urology, 2000, pp. 45-48, 85, Suppl 2.
Endothelin Inhibitors: Exploring Novel Therapeutics, Symposium, Jun. 7-8, 1999, Washington, D.C., Iddb Meeting Report, Jun. 25, 1999.
Boven, E., American Society of Clinical Oncology—35th Annual Meeting (Part 1), Symposium, May 15-18, 1999, Atlanta, GA, Iddb Meeting Report, Sep. 13, 2001.
McKinnon, C., American Society of Clinical Oncology-35th Annual Meeting (Part IV), Symposium, May 15-18, 1999, Atlanta, GA, Iddb Meeting Report, Sep. 13, 2001.
Adeniyi, A., American Urological Association-94th Annual Meeting, Symposium, May 1-6, 1999, Dallas, TX, Iddb Meeting Report, Aug. 26, 1999.
McKinnon, C., Topoisomerase inhibitors and other new agents, ID Drugs, 1999, pp. 629-632, vol. 2, No. 7.
Adeniyi, A., American Urological Association-94th Annual Meeting May 1-6, 1999, Dallas, TX, ID Drugs, 1999, pp. 656-658 vol. 2, No. 7.
Boven, E., American Society of Clinical Oncology-35th Annual Meeting, May 15-18, 1999, Atlanta, GA, ID Drugs, 1999, pp. 617-619, vol. 2, No. 7.
Nelson, Joel B., Editorial: Endothelin Receptor Antagonists in the Treatment of Prostate Cancer, The Prostate, pp. 91-92, 2001, vol. 49.
Nelson, Joel B., The Role of the Endothelin Axis in Prostate Cancer, The Prostate Journal, pp. 126-130, 1999, vol. 1, No. 3.
Nelson, Joel B. et al, Identification of endothelin-1 in the pathophysiology of metastatic adenocarcinoma of the prostate, Nature Medicine, pp. 944-949, Sep. 1995, vol. 1, No. 9.
Carducci, Michael A. et al, Endothelin Receptor Antagonist, ABT-627, For Prostate Cancer: Initial Trial Results, The Journal of Urology, p. 176, 1999, vol. 161(4) Suppl.
Jarvis, Michael F., et al., ABT-627, an endothelin ETA receptor-selective antagonist, attenuates tactile allodynia in a diabetic rat model of neuropathic pain, European Journal of Pharmacology, pp. 29-35, 2000, vol. 388. No. 1.
Bagnato, Anna, et al., Autocrine Actions of Endothelilin-1 as a Growth Factor in Human Ovarian Carcinoma Cells, Clinical Cancer Research, 1995, pp. 1059-1066, vol 1.
Wu-Wong, Jinshyun R., Endothelin attenuates apoptosis in human smooth muscle cells, Biochemical Journal, pp. 733-737, 1997, vol. 328.
Spinella, Francesca, et al., Endothelin-1 Induces Vascular Endothelial Growth Factor by Increasing Hypoxia-inducible Factor-1a in Ovarian Carcinoma Cells, The Journal of Biological Chemistry, pp. 27850-27855, Aug. 2, 2002, vol. 277, No. 31.
Kroodsma, J.M., et al., Endothelinen: modelijk een nieuw farmacologisch aangrijpingspunt bij hartvaatziekten, nierziekten en oncologische aandoingen, Nederlands Tijdschrift Voor Geneeskunde, 1997, pp. 1806-1810, vol. 141, Part 38.
Nelson, Joel B. et al., Endothelin-1 Production and Decreased Endothelin B Receptor Expression in Advanced Prostate Cancer, Journal of Cancer Research, Feb. 15, 1996, pp. 663-668, vol. 56.
Derwent AN 2001-565331, XP002271565.
Piettre, Serge R., et al., Monoaryl- and Bisaryldihydroxytropolones as Potent Inhibitors of Inositol Monophosphatase, Journal of Medicinal Chemistry, 1997, pp. 4208-4221, vol. 40.

* cited by examiner

PROTECTED FORMS OF N-(3-METHOXY-5-METHYLPIPERAZIN-2-YL)-2-(4-[1,3,4,-OXADIAZOL-2-YL]PHENYL)-PYRIDINE-3-SULPHONAMIDE

CROSS-REFERENCE TO RELATED APPLICATIONS

This application is a US National Stage under 35 U.S.C § 371 of International Application No. PCT/GB2005/000567 (filed 17 Feb. 2005) which claims priority under 35 U.S.C. § 119(a)-(d) to Application No. GB 0403744.6 filed on 20 Feb. 2004.

The present invention relates to an improved chemical process for preparing intermediates. Certain of these intermediates are useful in the manufacture of compounds which are useful in the treatment of, for example, cancer, pain and cardiovascular diseases in a warm-blooded animal such as man, particularly compounds which possess endothelin receptor antagonist activity.

In particular, the present invention relates to a chemical process for preparing [4-(1,3,4-oxadiazol-2-yl)phenyl]boronic acid which is used in the manufacture of N-(3-methoxy-5-methylpyrazin-2-yl)-2-(4-[1,3,4-oxadiazol-2-yl]phenyl)pyridine-3-sulphonamide which compound is disclosed as Example 36 of International Patent Application WO96/40681. This compound possesses endothelin receptor antagonist activity, and accordingly is useful whenever such antagonist activity is desired, such as for research tools within pharmacological, diagnostic, and related studies or in the treatment of diseases and medical conditions including, but not limited to hypertension, pulmonary hypertension, cardiac or cerebral circulatory disease and renal disease. In addition this compound is also useful in the treatment of cancer and pain, in a warm-blooded animal such as man.

A route for preparing N-(3-methoxy-5-methylpyrazin-2-yl)-2-(4-[1,3,4-oxadiazol-2-yl]phenyl)pyridine-3-sulphonamide is disclosed in International Patent Applications WO 96/40681 and WO 98/40332. The route involves the use of the compound N-(isobutoxycarbonyl)-2-(4-methoxycarbonylphenyl)-N-(3-methoxy-5-methylpyrazin-2-yl)pyridine -3-sulphonamide as an intermediate with the formation of the 1,3,4-oxadiazole in the 4-position of the phenyl group occurring at the end of the synthesis. This existing route is satisfactory for the synthesis of relatively small amounts of N-(3-methoxy-5-methylpyrazin-2-yl) -2-(4-[1,3,4-oxadiazol-2-yl]phenyl)pyridine-3-sulphonamide but is a linear rather than convergent synthesis, involving the isolation of a substantial number of intermediates. As such, the overall yield of this synthesis is not high.

Furthermore, as the heteroaryl moiety at the 4-position of the phenyl group is formed as the last step, it is necessary to undergo a linear synthesis approach with the rest of the molecule made first. This is clearly undesirable when substituents in distinct parts of the molecule need to be varied in order to investigate structure-activity relationships. It would be highly desirable if a convergent approach to the synthesis of this type of compound could be devised. This would also be of significant benefit in the efficiency of manufacturing large scale amounts of N-(3-methoxy-5-methylpyrazin-2-yl)-2-(4-[1,3,4-oxadiazol-2-yl]phenyl)pyridine-3-sulphonamide.

We have now devised a much improved process for the manufacture of heteroaryl-phenyl boronic acids, in particular, [4-(1,3,4-oxadiazol-2-yl)phenyl]boronic acid. The process allows exploitation of a more convergent route to N-(3-methoxy-5-methylpyrazin -2-yl)-2-(4-[1,3,4-oxadiazol-2-yl]phenyl)pyridine-3-sulphonamide than the previously described route and allows a reduction in the number of intermediates that must be isolated. This provides significant advantages of time and cost of manufacture.

In a further aspect of the present invention one of the heteroaryl-phenyl boronic acids, [4-(1,3,4-oxadiazol-2-yl) phenyl]boronic acid, produced according to the present invention, is used to prepare N-protected N-(3-methoxy-5-methylpyrazin-2-yl)-2-(4-[1,3,4-oxadiazol-2-yl]phenyl)pyridine-3-sulphonamides, in particular N-(isobutoxycarbonyl) N-(3-methoxy-5-methylpyrazin-2-yl)-2-(4-[1,3,4-oxadiazol-2-yl]phenyl)pyridine-3-sulphonamide. These intermediates may then be deprotected to form N-(3-methoxy-5-methylpyrazin-2-yl)-2-(4-[1,3,4-oxadiazol-2-yl]phenyl)pyridine-3-sulphonamide.

The process for the manufacture of heteroaryl-phenyl boronic acids of the present invention utilises the increased acidity of the heteroaryl ring proton, and involves the sequential use of two bases. Initial attempts at adding one equivalent of a base to a heteroaryl-phenyl bromo compound in order to induce halogen-metal exchange led to competing deprotonation of the heteroaryl ring. On quenching with a borate ester, a negligible yield of the desired product was achieved, together with starting material and by-products. The present inventors found, surprisingly, that the sequential use of two bases leads to good yields of the desired heteroaryl-phenyl boronic acids. In the process of the present invention the heteroaryl ring is initially deprotonated with a (typically) "weaker" base, before inducing halogen-metal exchange with a (typically) "stronger" base.

According to a first aspect of the present invention, there is provided a process for the preparation of a compound of the Formula I

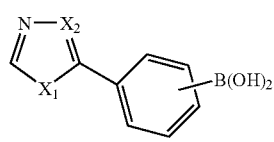

(I)

wherein,
$X_1$ is selected from O, $NR_1$ or S; and
$X_2$ is selected from CH or N;
wherein $R_1$ is a nitrogen-protecting group,
which comprises:—
the sequential reaction of a compound of the Formula II

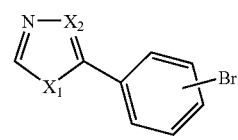

(II)

with,
(i) methyl- or an optionally substituted aryl-lithium; and then
(ii) n-butyl-, s-butyl-, t-butyl- or n-hexyl-lithium; and then
(iii) a borate ester.

For process steps (i), (ii) and (iii), the reactions may conveniently be carried out in an inert solvent or diluent or an ethereal solvent such as diethyl ether, tetrahydrofuran, diethoxymethane, 1,2-dimethoxyethane or 1,4-dioxan. Thus, for example, the reaction may be carried out by sequentially treating 2-(4-bromophenyl)-1,3,4-oxadiazole with 4-methylphenyllithium, followed by n-hexyllithium, and finally tri-isopropylborate in a suitable solvent or diluent, for example, an ethereal solvent such as tetrahydrofuran, at a temperature in the range, for example, −90 to −50° C., more particularly −70 to −55° C., conveniently at or near −70° C.

Optionally the heteroaryl-phenyl bromo compound of Formula II can be charged to a solution of the first base to enable deprotonation, followed by the addition of the second base to induce transmetallation. This method although slightly less efficient in yield and quality does have advantages in cases where the first base must be generated in situ due to lack of stability at ambient temperatures. In this case only one cryogenic vessel is required to complete the processing.

The molar ratios of the reagents used in process steps (i), (ii), and (iii), are preferably in the range from 1.0-1.5:1.0-1.5:2.1-3 respectively, but more preferably in the range 1.06-1.3:1.07-1.1:2.2-2.3 respectively. Conveniently, the lithiated intermediates formed during the conversion of compounds of the Formula II to compounds of Formula I are not isolated as such but are each prepared and used as a solution in an organic solvent. Thereby, compounds of Formula I may be manufactured from compounds of Formula II in a one-pot procedure.

An aryl lithium is, for example, phenyl or naphthyl-lithium.

An optional substituent for an aryl lithium is, for example, methyl.

Particularly preferred optionally substituted aryl lithiums are, for example, phenyl-, 2-methylphenyl-, 4-methylphenyl-, mesityl- or naphthyl-lithium.

A borate ester is an alkyl, alkenyl or aryl boronic ester, for example, trimethyl-, triethyl- or triisopropyl-borate.

When $R_1$ is a nitrogen-protecting group, then, for example, suitable methods for protection are those known to those skilled in the art. Conventional protecting groups may be used in accordance with standard practice (for illustration see T. W. Green, Protective Groups in Organic Synthesis, John Wiley and Sons, 1991).

A suitable nitrogen-protecting group, $R_1$, is, for example, an (1-6C)alkyl, phenyl, allyl, methoxymethyl, benzyl, triphenylmethyl or diphenylphosphinyl protecting group.

This first aspect of the present invention provides compounds of Formula I in commercially acceptable yields and of high quality.

Further values of $X_1$ and $X_2$ are as follows. Such values may be used where appropriate with any definitions, claims or embodiments defined hereinbefore or hereinafter.

$X_1$ is O.
$X_1$ is $NR_1$
$X_1$ is S.
$X_2$ is CH.
$X_2$ is N.
$X_1$ is O, and $X_2$ is CH.
$X_1$ is O, and $X_2$ is N.
$X_1$ and $X_2$ are N.
$X_1$ is $NR_1$, and $X_2$ is CH.
$X_1$ is $NR_1$, and $X_2$ is N.
$X_1$ is S and $X_2$ is CH.
$X_1$ is S and $X_2$ is N.
$R_1$ is allyl or benzyl.
$R_1$ is benzyl.

Therefore in an additional aspect of the invention there is provided a process for the preparation of compounds of the Formula I

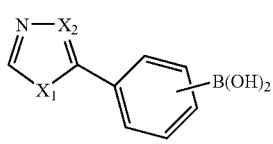

wherein,
$X_1$ is selected from O, $NR_1$ or S; and
$X_2$ is selected from CH or N;

wherein $R_1$ is a nitrogen-protecting group;
which comprises:—
the sequential reaction of compounds of the Formula II

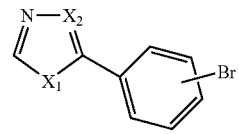

with,
(i) 4-methylphenyllithium; and then
(ii) n-hexyllithium; and then
(iii) triisopropylborate.

In a further aspect of the invention there is provided a process for the preparation of compounds of the Formula I

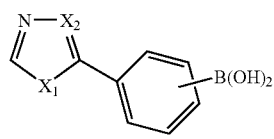

wherein,
$X_1$ is selected from O, $NR_1$ or S; and
$X_2$ is selected from CH or N;
wherein $R_1$ is a nitrogen-protecting group; which comprises:—
the sequential reaction of compounds of the Formula II

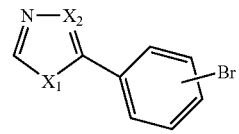

with,
(i) methyllithium; and then
(ii) n-hexyllithium; and then
(iii) triisopropylborate.

In a further aspect of the invention there is provided a process for the preparation of compounds of the Formula I

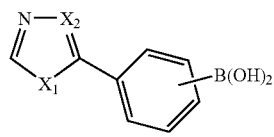

wherein,
$X_1$ is O; and
$X_2$ is N;
which comprises:—
the sequential reaction of compounds of the Formula II

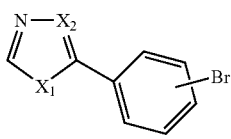
(II)

with,
(i) methyllithium; and then
(ii) n-butyllithium; and then
(iii) triisopropylborate.

In a further aspect of the invention there is provided a process for the preparation of compounds of the Formula I,

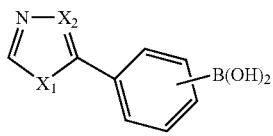
(I)

wherein,
$X_1$ is O; and
$X_2$ is N;
which comprises:—
the sequential reaction of compounds of the Formula II

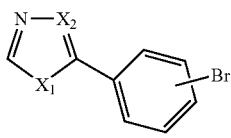
(II)

with,
(i) 4-methyphenyllithium; and then
(ii) n-butyllithium; and then
(iii) triisopropylborate.

Compounds of the formula (II) may be prepared according to the experimental methods and procedures disclosed in *Bioorganic & Medicinal Chemistry Letters*, 2002, 12 (20), 2879-2882; *Eur. J. Med. Chem.*, 2000, 35, 157-162; *Helvetica Chimica Acta*, 1950, 33, 1271-1276; *Eur. J. Med. Chem.*, 1985, 20 (3), 257-66 and *J. Het. Chem.*, 1989, 26, 1341.

A further aspect of the present invention provides the use of [4-(1,3,4-oxadiazol-2-yl)phenyl]boronic acid, prepared according to the present invention, in the preparation of compounds of Formula IV which are intermediates useful in the preparation of N-(3-methoxy-5-methylpyrazin-2-yl)-2-(4-[1,3,4-oxadiazol-2-yl]phenyl)pyridine-3-sulphonamide.

N-(3-Methoxy-5-methylpyrazin-2-yl)-2-(4-[1,3,4-oxadiazol-2-yl]phenyl)pyridine-3-sulphonamide is prepared by deprotecting compounds of Formula IV.

In this aspect of the invention [4-(1,3,4-oxadiazol-2-yl)phenyl]boronic acid is coupled with compounds of Formula III to form compounds of Formula IV.

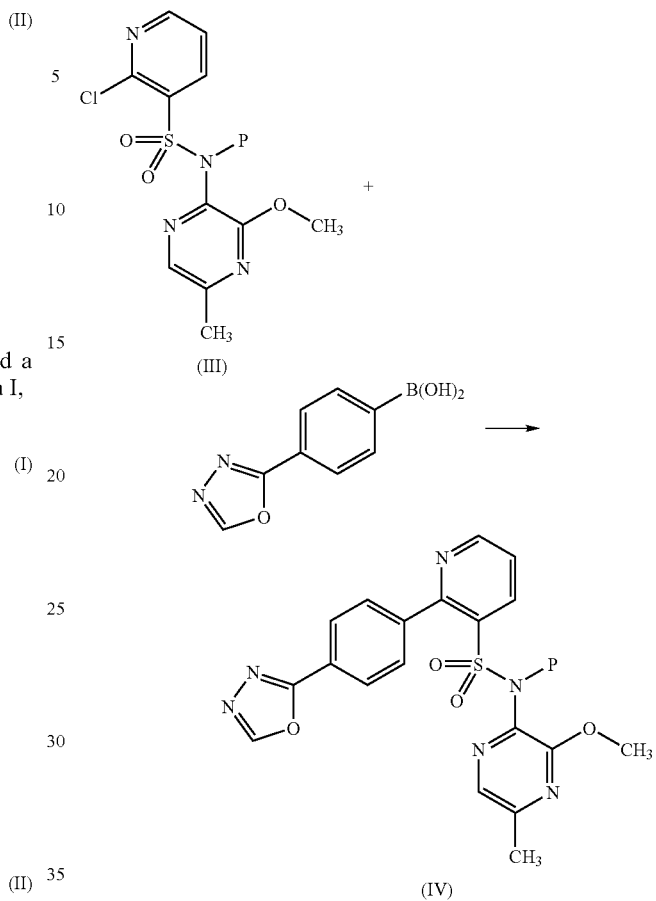

Particularly this reaction takes place in an aqueous solvent, for example methanol, ethanol, isopropanol, industrial methylated spirit (IMS), isobutanol, NMP (N-methylpyrrolidinone), DMF; with or without an organic phase, for example toluene or xylenes at a temperature in the range, for example 60 to 100° C. more particularly 75 to 85° C., in the presence of:
(i) the boronic acid
(ii) a suitable source of palladium (0), for example $PdCl_2$, $Pd(Ph_3P)_4$ or $Pd(OAc)_2$;
(iii) a suitable ligand, for example triphenylphosphine or 3,3',3"-phosphinidyne tris(benzenesulphonic acid) trisodium salt;
(iv) a base, for example triethylamine, benzyldimethylamine, N-methylmorpholine, N-methylpiperidine, triethanolamine, ethyldiethanolamine, diisopropylethylamine, potassium acetate, cesium fluoride or potassium fluoride.

Particularly the source of palladium is palladium acetate.
Particularly the base is N-methylmorpholine. In another aspect, particularly the base is triethylamine.

Particularly this reaction takes place in an aqueous solvent without an organic phase. In another aspect, particularly this reaction takes place in an aqueous solvent with an organic phase. Where this reaction takes place in an aqueous solvent with an organic phase, particularly the organic phase comprises toluene. In another aspect of the present invention, where this reaction takes place in an aqueous solvent with an organic phase, particularly the organic phase comprises xylene.

In another aspect, this reaction more specifically takes place in the presence of palladium acetate, 3,3',3''-phosphinidyne tris(benzenesulphonic acid) trisodium salt, N-methylmorpholine in water and isopropanol.

In another aspect, this reaction more specifically takes place in the presence of palladium acetate, 3,3',3''-phosphinidyne tris(benzenesulphonic acid) trisodium salt, triethylamine, xylene, water and IMS.

The molar ratios of the reagents used in process steps (i), (ii), (iii) and (iv), are preferably in the range from 1.0-2.0: 0.02-0.3:0.06-0.9:1.5-5.0 respectively, but more preferably in the range 1.4-1.6:0.03-0.1:0.09-0.3:2.0-3.0 respectively.

In compounds of Formula III or Formula IV, P is a nitrogen-protecting group. Suitable methods for protection are those known to those skilled in the art. Conventional protecting groups may be used in accordance with standard practice (for illustration see T. W. Green, Protective Groups in Organic Synthesis, John Wiley and Sons, 1991).

A suitable value for P is, for example, an acyl group, for example a $C_{1-6}$alkanoyl group such as acetyl; an aroyl group, for example benzoyl; a $C_{1-6}$alkoxycarbonyl group, for example a methoxycarbonyl, ethoxycarbonyl, isobutoxycarbonyl or tert-butoxycarbonyl group; an arylmethoxycarbonyl group, for example benzyloxycarbonyl; a phosphinyl group, for example diphenylphosphinyl; a benzyl group or a $C_{2-6}$alkenyl group such as allyl.

A suitable value for P is a $C_{1-6}$alkoxycarbonyl group. More suitable values for P are a methoxycarbonyl, ethoxycarbonyl or isobutoxycarbonyl group. More specifically a value for P is isobutoxycarbonyl.

The deprotection conditions for the nitrogen protecting groups described herein necessarily vary with the choice of protecting group. Thus, for example, an acyl group such as a $C_{1-6}$alkanoyl or a $C_{1-6}$alkoxycarbonyl group or an aroyl group may be removed for example, by hydrolysis with a suitable base such as an alkali metal hydroxide, for example lithium or sodium hydroxide or an amine, for example ammonia. Alternatively an alkoxycarbonyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A phosphinyl group may be removed by base hydrolysis such as an alkali metal hydroxide, for example lithium or sodium hydroxide or an amine, for example ammonia. A benzyl group may be removed by hydrogenation over a catalyst such as palladium-on-carbon. A $C_{2-6}$alkenyl group such as allyl may be removed palladium assisted hydrolysis.

In a further aspect of the invention there is provided a process for preparing a compound of Formula IV which comprises reacting [4-(1,3,4-oxadiazol-2-yl)phenyl]boronic acid with a compound of Formula III.

In a further aspect of the invention there is provided a process for preparing a compound of Formula IV which comprises reacting [4-(1,3,4-oxadiazol-2-yl)phenyl]boronic acid, prepared according to the present invention, with a compound of Formula III.

In this aspect of the invention, more specifically the invention provides the use of [4-(1,3,4-oxadiazol-2-yl)phenyl]boronic acid, prepared according to the present invention, in the preparation of N-(isobutoxycarbonyl) N-(3-methoxy-5-methylpyrazin- 2 - yl) -2-(4-[1,3,4-oxadiazol-2-yl]phenyl)pyridine-3-sulphonamide a compound of Formula IV and an intermediate useful in the preparation of N-(3-methoxy-5-methylpyrazin-2-yl) -2-(4-[1,3,4-oxadiazol-2-yl]phenyl)pyridine-3-sulphonamide.

In this aspect of the invention [4-(1,3,4-oxadiazol-2-yl)phenyl]boronic acid is coupled with N-(isobutoxycarbonyl)-2-chloro-N-(3-methoxy-5-methylpyrazin -2-yl)pyridine-3-sulphonamide to form N-(isobutoxycarbonyl) N-(3-methoxy-5-methylpyrazin-2-yl)-2-(4-[1,3,4-oxadiazol -2-yl]phenyl)pyridine-3-sulphonamide.

The preparation of N-(isobutoxycarbonyl)-2-chloro-N-(3-methoxy- 5- methylpyrazin-2-yl)pyridine-3-sulphonamide is described in Example 1 of WO96/40681.

Thus according to this aspect of the invention there is provided a process for preparing N-(isobutoxycarbonyl) N-(3-methoxy-5-methylpyrazin-2-yl)-2-(4-[1,3,4-oxadiazol-2-yl]phenyl)pyridine-3-sulphonamide which comprises coupling [4-(1,3,4-oxadiazol-2-yl)phenyl]boronic acid with N-(isobutoxycarbonyl)-2-chloro-N-(3-methoxy -5-methylpyrazin-2-yl)pyridine-3-sulphonamide.

Therefore in a further aspect of the invention there is provided the use of [4-(1,3,4-oxadiazol-2-yl)phenyl]boronic acid in the preparation of N-(isobutoxycarbonyl) N-(3-methoxy-5-methylpyrazin-2-yl)-2-(4-[1,3,4-oxadiazol-2-yl]phenyl)pyridine-3-sulphonamide.

In a further aspect of the invention there is provided the use of [4-(1,3,4-oxadiazol-2-yl)phenyl]boronic acid, prepared according to the process of the present invention, in the preparation of N-(isobutoxycarbonyl) N-(3-methoxy-5-methylpyrazin-2-yl) -2-(4-[1,3,4-oxadiazol-2-yl]phenyl)pyridine-3-sulphonamide.

In a further aspect of the invention there is provided a compound of Formula IV.

In a further aspect of the invention there is provided N-(isobutoxycarbonyl) N-(3-methoxy -5-methylpyrazin-2-yl)-2-(4-[1,3,4-oxadiazol-2-yl]phenyl)pyridine-3-sulphonamide.

In a further aspect of the invention there is provided the use of N-(isobutoxycarbonyl) N-(3-methoxy-5-methylpyrazin-2-yl)-2-(4-[1,3,4-oxadiazol-2-yl]phenyl)pyridine-3-sulphonamide in the preparation of N-(3-methoxy-5-methylpyrazin-2-yl)-2-(4-[1,3,4-oxadiazol-2-yl]phenyl)pyridine-3-sulphonamide.

The invention will now be illustrated by the following non-limiting Examples in which, unless otherwise stated:—
(i) yields are intended for the assistance of the reader only and are not necessarily the maximum attainable by diligent process development;
(ii) $^1$H NMR spectra were determined at either 270 MHz or 400 MHz in $DMSOd_6$ using tetramethylsilane (TMS) as an internal standard, and are expressed as chemical shifts (delta values) in parts per million relative to TMS using conventional abbreviations for designation of major peaks: s, singlet; m, multiplet; t, triplet; br, broad; d, doublet.

EXAMPLE 1

[4-(1,3,4-oxadiazol-2-yl)phenyl]boronic acid

A solution of methyllithium (8% w/w in diethoxymethane) (65 ml) was added to a suspension of 2-(4-bromophenyl)-1, 3,4-oxadiazole (40 g) in tetrahydrofuran (THF) (415 ml) at −65° C. After an hour a solution of n-butyllithium (2.5M in hexanes) (78 ml) was then added at −65° C. After an hour, triisopropylborate (90 ml)) was then added maintaining the reaction mixture at −65° C. The reaction mixture was held at −65° C. for an hour and then warmed to −20° C. and drowned out into a mixture of acetic acid (28 ml) in water (222 ml). The resultant solid was isolated, washed with THF and water, and dried to yield the title compound (28.96 g@ 95.1% w/w, 82%); 400 MHz NMR Spectrum: ($DMSOd_6$) 8.00 (s, 4H), 8.31 (s, 2H), 9.35 (s, 1H); Mass Spectrum MH$^+$ 191.0628 (calc. using 11-B) Found 191.0633.

The 2-(4-bromophenyl)-1,3,4-oxadiazole used as a starting material was prepared as follows:

To a suspension of 4-bromobenzoic hydrazide (200 g) in industrial methylated spirit (700 ml) was added triethylorthoformate (309 ml), industrial methylated spirit (100 ml) and sulphuric acid (0.8 ml). The reaction mixture was heated to reflux for 1 hour. The reaction mixture was cooled to 0-5° C. and product crystallised. Product was isolated, washed and dried to yield 2-(4-bromophenyl)-1,3,4-oxadiazole (186.1 g, 89.9%). 400 MHz NMR Spectrum: (DMSOd$_6$) 9.35 (s, 1H), 7.98 (d, 1H), 7.95 (d, 1H), 7.84 (d, 1H), 7.81 (d, 1H); Mass Spectrum MH$^+$ 224.9663 (calc. using 79-Br) Found 224.9701.

EXAMPLE 2

[4-(1,3,4-oxadiazol-2-yl)phenyl]boronic acid

Lithium granules (8.2 g) and tetrahydrofuran (670 g) were charged to a reactor under an argon atmosphere and the mixture cooled to −35° C. 4-Chlorotoluene (74.3 g) was added at −35° C. and the mixture was held at this temperature for 6 hours. The resultant solution was added to a suspension of 2-(4-bromophenyl)-1,3,4-oxadiazole (124.4 g) in tetrahydrofuran (800 g) at −65° C. After 30 mins a solution of n-hexyllithium (33% w/w in hexanes) (240 ml) was then added at −65° C. After a further 30 min triisopropylborate (230.8 g) was then added maintaining the reaction mixture at −65° C. The reaction mixture was allowed to warm to −35° C. and drowned out into a solution of acetic acid (91.5 g) in water (688 g). The resultant solid was isolated, washed with THF and water, and dried to yield the title compound (92.2 g, 88%).

EXAMPLE 3

[4-(1,3,4-oxadiazol-2-yl)phenyl]boronic acid

Example 2 was repeated but the charge of 4-chlorotoluene increased from 1.06 moles to 1.30 moles. The yield of the title compound increased to 89.3%.

EXAMPLE 4

[4-(1,3,4-oxadiazol-2-yl)phenyl]boronic acid

Tetrahydrofuran (250 g) was charged to a mixture of lithium granules (3.02 g) and biphenyl (0.01 g) under an argon atmosphere and the mixture cooled to −30° C. 2-Chlorotoluene (27.55 g) was slowly added at −30° C. The reaction was held at −30° C. for 6 hours and then cooled to −65° C. A mixture of 2-(4-bromophenyl)-1,3,4-oxadiazole (50.0 g) in THF (300 g) was slowly added at −65° C. The reaction was held at −65° C. for 30 minutes then a solution of n-hexyllithium (33% w/w in hexanes, 86 ml) was added at −65° C. The reaction was held at −65° C. for 30 minutes and then trimethylborate (48.7 g) was added at −65° C. The reaction was held at −65° C. for 10 minutes then methanol (55.3 g) was added followed by 4-methyl-2-pentanone (240 g). The reaction mixture was warmed and the low boiling solvents distilled off under vacuum to a maximum temperature of 55° C. The residual mixture was cooled to 0° C. and 10% w/w sulphuric acid (92 g) was added followed by water (92 g) whilst maintaining the temperature below 7° C. Product precipitated. The pH was adjusted to 6.5 by the addition of more 10% w/w sulphuric acid (85.3 g). The mixture was heated to 40° C. then cooled back to 5-10° C. Product was isolated and washed with THF (56 g) and water (60 g), yielding wet title compound (25.2 g, 60%).

EXAMPLE 5

[4-(1,3,4-oxadiazol-2-yl)phenyl]boronic acid

Tetrahydrofuran was charged to lithium granules (7.6 g) under an argon atmosphere and the mixture cooled to −30° C. 2-Chlorotoluene (69.4 g) was slowly added at −30° C. The reaction was held at −30° C. for 6 hours then added to a suspension of 2-(4-bromophenyl)-1,3,4-oxadiazole (124.4 g) in tetrahydrofuran (800 g) at −65° C. The reaction was held at −65° C. for 30 minutes then a solution of n-hexyllithium (33% w/w in hexanes, 245 ml) was added at −65° C. The reaction was held at −65° C. for 30 minutes and then trimethylborate (230.8 g) was added at −65° C. The reaction was held at −65° C. for 30 minutes then methanol (175 ml) was added followed by 4-methyl-2-pentanone (600 g). The reaction mixture was warmed and the low boiling solvents distilled off under vacuum to a maximum temperature of 50° C. The reaction mixture was cooled to 5-10° C. and the pH adjusted to 6.5 by the addition of 5% w/w sulphuric acid (990.5 g). Product precipitated. The mixture was heated to 40° C. then cooled back to 10° C. Product was isolated, washed with THF and water, and dried yielding the title compound (79.3 g, 75.5%).

EXAMPLE 6

[4-(1,3,4-oxadiazol-2-yl)phenyl]boronic acid

Example 4 was repeated but chlorobenzene (61.6 g) was used instead of 2-chlorotoluene. The isolated yield of the title compound was 87.8 g, (83.8%).

EXAMPLE 7

N-(Isobutoxycarbonyl) N-(3-methoxy-5-methylpyrazin-2-yl)-2-(4-[1,3,4-oxadiazol-2-yl]phenyl) Pyridine-3-sulphonamide Palladium acetate (0.4144 g) and 3,3',3"-phosphinidyne tris(benzenesulphonic acid) trisodium salt 30% w/w aq sol (3.26 g) were dissolved in water (35 ml) over 6 minutes in an ultrasonic bath. The yellow solution was added to a stirred slurry of [4-(1,3,4-oxadiazol-2-yl)phenyl]boronic acid (10 g) and isobutyl [(2-chloropyridin-3-yl)sulfonyl](3-methoxy-5-methylpyrazin-2-yl)carbamate (16.86 g) in xylene (100 ml), industrial methylated spirit (50 ml) and triethylamine (17 ml). The catalyst dissolution flask was then washed in with water (5 ml) and the reaction mixture heated to reflux (80° C.) on an oil bath (105° C.) and stirred at reflux for 24.5 hours. The reaction mixture was cooled to 30° C. and filtered through a Whatman GF/B glass filter paper and the lower aqueous phase separated off. The reaction flask and filter cake was washed with xylene (20 ml). The xylene wash was used to re-extract the aqueous phase. The combined organic phases were stirred and heated to reflux (85° C.) in a clean 500 ml 4-necked flask equipped with overhead stirrer, water condenser, and nitrogen atmosphere. Essochem solvent 30 (hydrocarbons Bp 100-130° C.) (100 ml) was added dropwise over 6 min and the mixture was allowed to self cool to ambient temperature and then further cooled to −5° C. and held for 1 hour. The product was filtered off and washed with Essochem solvent 30 (50 ml). The cake was dried on the filter for 3 hours to give 15.20 g@100% strength, yield 76.8%. 270 MHz $^1$H-NMR Spectrum: 0.70 (d, 6H), 1.72 (m, 1H), 2.51 (s, 3H), 3.84 (d, 2H), 4.00 (s, 3H), 7.59 (m, 1H); 7.80 (d, 2H), 7.90 (s, 1H), 8.17 (d, 2H), 8.50 (s, 1H), 8.90 (m, 1H) and 9.00 (d, 1H). Mass Spectrum MH$^+$=525.2 ($C_{24}H_{25}N_6O_6S$=525.16).

EXAMPLE 8

N-(Isobutoxycarbonyl) N-(3-methoxy-5-methylpyrazin-2-yl)-2-(4-[1,3,4-oxadiazol-2-yl]phenyl) pyridine-3-sulphonamide To a nitrogen purged 500 mL multi necked flask equipped with an overhead stirrer was charged isobutyl [(2-chloropyridin-3-yl)sulfonyl](3-methoxy-5-methylpyrazin-2-yl)carbamate (22.15 g), [4-(1,3,4-oxadiazol-2-yl)phenyl]boronic acid (12.26 g), isopropanol (60 ml), water (140 ml) and 3,3',3"-phosphinidyne tris(benzenesulphonic acid) trisodium salt 30% w/w aq sol (13.7 g). Agitation was started and palladium acetate (0.541 g) was added after 10 minutes. N-Methylmorpholine (13.25 ml) was added and the temperature was adjusted to 80° C. After 4 h 20 min toluene (140 ml) was added and the temperature adjusted to 60° C. After a further 45 min the mixture was filtered through a 1 μm glass fibre filter paper and the aqueous phase separated off. The reaction flask and filter cake was washed with toluene (22 ml). The toluene wash was used to re-extract the aqueous phase and the organic layers were combined. These contained the title compound (22.8 g, 90%) which was not isolated.

EXAMPLE 9

N-(Isobutoxycarbonyl) N-(3-methoxy-5-methylpyrazin-2-yl)-2-(4-[1,3,4-oxadiazol-2-yl]phenyl) pyridine-3-sulphonamide To a nitrogen purged 150 ml multi necked flask equipped with an overhead stirrer was charged isobutyl [(2-chloropyridin-3-yl)sulfonyl](3-methoxy-5-methylpyrazin-2-yl)carbamate (7.75 g), [4-(1,3,4-oxadiazol-2-yl)phenyl]boronic acid (4.29 g), isopropanol (21 ml), water (49 ml) and 3,3',3"-phosphinidyne tris(benzenesulphonic acid) trisodium salt 30% w/w aq sol (2.88 g). Agitation was started and palladium acetate (0.114 g) was added after 10 minutes. Potassium fluoride (2.48 g) was added and the temperature was adjusted to 80° C. After 5 h toluene (49 ml) was added and the temperature adjusted to 60° C. After a further 10 min the mixture was filtered through a 1 μm glass fibre filter paper and the aqueous phase separated off. The organic phase contained the title compound (7.36 g, 83%) which was not isolated.

The invention claimed is:

1. A compound of Formula IV:

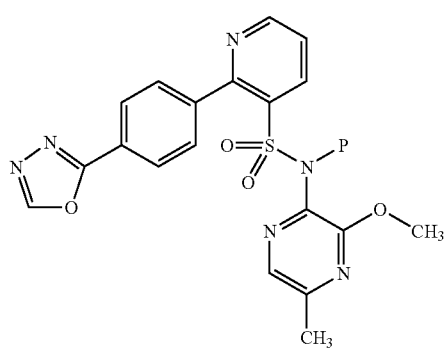

(IV)

wherein P is a $C_{1-6}$alkanoyl group, an aroyl group, a $C_{1-6}$alkoxycarbonyl group or an arylmethoxycarbonyl group.

2. A compound of Formula IV as claimed in claim 1 which is N-(isobutoxycarbonyl) N-(3-methoxy-5-methylpyrazin-2-yl)-2-(4-[1,3,4-oxadiazol-2-yl]phenyl) pyridine-3-sulphonamide.

3. A compound of Formula IV as claimed in claim 1 wherein P is a $C_{1-6}$alkoxycarbonyl group.

4. A compound of Formula IV as claimed in claim 3 which is N-(isobutoxycarbonyl) N-(3-methoxy-5-methylpyrazin-2-yl)-2-(4-[1,3,4-oxadiazol-2-yl]phenyl)pyridine-3-sulphonamide.

5. A process for preparing compounds of Formula IV:

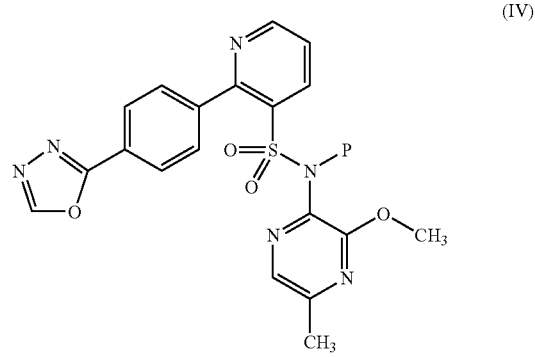

(IV)

which comprises coupling [4-(1,3,4-oxadiazol-2-yl)phenyl]boronic acid with a compound of Formula III:

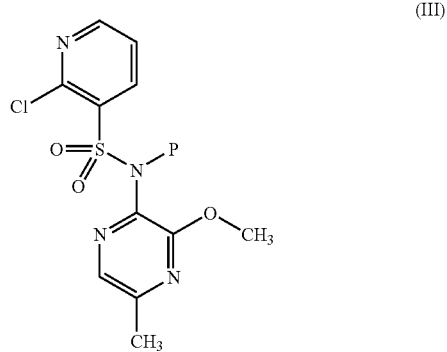

(III)

wherein P is a nitrogen-protecting group which takes place in the presence of
(i) a source of palladium (0) selected from $PdCl_2$, $Pd(Ph_3P)_4$ or $Pd(OAc)_2$;
(ii) a suitable ligand selected from triphenylphosphine or 3,3',3"-phosphinidyne tris(benzenesulphonic acid) trisodium salt;
(iii) a base selected from triethylamine, benzyldimethylamine, N-methylmorpholine, N-methylpiperidine, triethanolamine, ethyldiethanolamine, diisopropylethylamine, potassium acetate, cesium fluoride or potassium fluoride.

6. The process according to claim 5 wherein P is isobutoxycarbonyl.

* * * * *

UNITED STATES PATENT AND TRADEMARK OFFICE
CERTIFICATE OF CORRECTION

PATENT NO. : 7,626,020 B2 Page 1 of 1
APPLICATION NO. : 10/598116
DATED : December 1, 2009
INVENTOR(S) : Butlin et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 435 days.

Signed and Sealed this

Second Day of November, 2010

David J. Kappos
*Director of the United States Patent and Trademark Office*